United States Patent
Laugharn, Jr.

(10) Patent No.: US 8,999,704 B2
(45) Date of Patent: Apr. 7, 2015

(54) METHOD AND APPARATUS FOR HEADSPACE CONTROL IN ACOUSTIC PROCESSING OF SAMPLES

(75) Inventor: James A. Laugharn, Jr., Winchester, MA (US)

(73) Assignee: Covaris, Inc., Woburn, MA (US)

( * ) Notice: Subject to any disclaimer, the term of this patent is extended or adjusted under 35 U.S.C. 154(b) by 555 days.

(21) Appl. No.: 13/186,858

(22) Filed: Jul. 20, 2011

(65) Prior Publication Data

US 2012/0015419 A1 Jan. 19, 2012

Related U.S. Application Data

(63) Continuation-in-part of application No. 12/489,693, filed on Jun. 23, 2009.

(60) Provisional application No. 61/075,137, filed on Jun. 24, 2008.

(51) Int. Cl.
*C12M 1/33* (2006.01)
*C12M 3/08* (2006.01)
*B01F 11/02* (2006.01)
*G01N 1/28* (2006.01)
*G01N 35/00* (2006.01)

(52) U.S. Cl.
CPC ............ *B01F 11/0283* (2013.01); *G01N 1/286* (2013.01); *B01J 2219/00308* (2013.01); *B01J 2219/00344* (2013.01); *B01J 2219/00486* (2013.01); *B01J 2219/00722* (2013.01); *B01J 2219/0074* (2013.01); *G01N 2035/00554* (2013.01)

(58) Field of Classification Search
CPC .......... C12M 1/33; C12M 47/06; C12M 1/42; C12N 1/066; B01L 2400/0487
USPC .................................... 435/173.7, 306.1
See application file for complete search history.

(56) References Cited

U.S. PATENT DOCUMENTS

| | | | |
|---|---|---|---|
| 4,891,654 A * | 1/1990 | Hoisington et al. | 347/40 |
| 4,930,532 A * | 6/1990 | Mayer | 134/184 |
| 6,515,030 B1 | 2/2003 | Bechtel et al. | |
| 7,147,692 B2 * | 12/2006 | Fornai et al. | 95/210 |
| 2002/0009015 A1 * | 1/2002 | Laugharn et al. | 366/108 |

FOREIGN PATENT DOCUMENTS

GB 2308182 A 6/1997
WO WO 2008/016691 A2 2/2008

OTHER PUBLICATIONS

International Search Report for International Application No. PCT/US2009/003719 mailed Oct. 23, 2009.
Written Opinion of the International Searching Authority for International Application No. PCT/US2009/003719 mailed Oct. 23, 2009.

* cited by examiner

*Primary Examiner* — Michael Hobbs
(74) *Attorney, Agent, or Firm* — Wolf, Greenfield & Sacks, P.C.

(57) ABSTRACT

Method and apparatus for controlling acoustic treatment of a sample including a liquid. A processing volume in which the sample is acoustically treated may be controlled, e.g., by positioning a suitable element so as to reduce and/or eliminate a headspace size at a sample/gas interface. An interaction between the acoustic energy and the sample may be controlled, e.g., by using a headspace control element positioned at least partially in the sample that helps to reduce splashing or other sample ejection that would otherwise occur.

32 Claims, 10 Drawing Sheets

METHOD AND APPARATUS FOR HEADSPACE CONTROL IN ACOUSTIC PROCESSING OF SAMPLES

This application is a continuation in part of U.S. application Ser. No. 12/489,693, filed Jun. 23, 2009, which claims priority to U.S. provisional application No. 61/075,137, filed Jun. 24, 2008.

BACKGROUND

1. Field of the Invention

Systems and methods for processing of samples with acoustic energy are generally disclosed.

2. Related Art

Acoustic energy-based sample processing devices, such as Adaptive Focused Acoustic apparatuses made by Covaris of Woburn, Mass., are effective for homogenization and disruption of biological tissues, cells and other sample material. The apparatus are also beneficial for chemical applications, such as compound dissolution, formulation, micronization, emulsification and other processes. With such devices, a controlled acoustic field enables repeatable processes to be developed which often result in higher recovery of target molecules. Such target molecules may be, for example, DNA, RNA, proteins, and the like. Target molecules or other materials may be contained as samples within a vessel.

SUMMARY OF INVENTION

In some cases, acoustic treatment of a sample causes cavitation or other disruption in the sample such that energy that would otherwise be directed to processing sample material is absorbed, reflected or otherwise wasted or left unused for processing the sample. For example, cavitation or other relatively violent motion in a sample caused by acoustic energy can cause a portion of a sample to be ejected from the sample and into other areas of a vessel holding the sample, such as on the vessel sidewall. Time spent by the ejected sample portion outside of an acoustic focal zone or other area where the sample portion can be subjected to suitable acoustic energy may cause the sample to be incompletely or otherwise improperly processed or result in a process that requires more time and/or energy than necessary to achieve the desired result. Indeed, in some cases, ejected sample material may stick to a vessel sidewall or other location outside of the main sample volume, thus resulting in the ejected material not be acoustically processed at all.

In addition, the inventor has unexpectedly found that such acoustic energy loss or waste can be caused by gas present in the sample interfering with the acoustic energy. Thus, the inventor has discovered that acoustic energy loss or otherwise inefficient acoustic processing can be substantially minimized by reducing an amount of gas that can be absorbed, dissolved or otherwise enter into a liquid portion of a sample. Without wishing to be bound to any particular theory, the inventor believes that acoustic processing of a sample that includes liquid, particularly at relatively higher energy levels, tends to disrupt the interface between the sample and a gas above the sample. This disruption, which in some cases may include turbulent motion at the interface, may cause transfer of gas into the sample liquid (e.g., such as by dissolution or other mechanism). Gas carried by the sample liquid (e.g., whether dissolved and/or in bubble form) may interfere with acoustic processing, such as by gas bubbles reflecting acoustic energy, an increase in gas bubbles present in the sample caused by release of dissolved gas from the liquid, increased pressure in collapsing cavitation bubbles reducing energy that would otherwise be directed to sample material, and/or potentially other mechanisms.

In accordance with one aspect of the invention, a headspace above a sample may be reduced in volume and/or a surface area presented to the sample. Reduction or other control of the headspace may in some arrangements provide the ability to reduce or eliminate ejection or other movement of sample material from a desired region in a vessel, may provide for more efficient transmission or use of acoustic energy in the sample material, or other features. For example, the inventor has found that reducing a headspace size for a sample (whether volume or surface area presented to a sample) can reduce the acoustic intensity or power and/or reduce processing time needed to achieve a desired result of the acoustic processing. For example, it has been found that processing of a 1.0 milliliter (ml) sample in the presence of a 0.9 ml headspace requires a power level of about 36 watts and a processing time of 60 minutes to cause a desired result (e.g., particle size reduction from 70 microns to 25 microns in this example). However, processing of a 1.9 ml sample volume of the same material (i.e., a larger volume) with a reduced headspace volume of less than 25 microliters at the same acoustic power level (e.g., 36 watts) has been found to achieve the same result in 15 minutes processing time. In some cases, more efficient acoustic processing is believed to be provided by reducing an amount of gas that is dissolved or otherwise entrained in the sample. By reducing the amount of gas in the sample, less gas may be present in the sample to be released into bubbles that reflect acoustic energy and/or to interfere with cavitation bubble collapse, etc. As a result, reducing a headspace size may be effective in reducing gas entrained into a sample during acoustic processing, thereby making the acoustic processing more efficient or otherwise more effective.

In one aspect of the invention, an acoustic treatment device includes a vessel having a total volume and arranged to hold a sample, and a sample including a liquid in the vessel, where the sample has a sample volume that is less than the total volume and defines an interface between the sample and a gas. An acoustic energy source may provide acoustic energy, having a focal zone, to the sample while the sample is in the vessel and is separated from the acoustic energy source, and a vessel holder may support the vessel at a location at least partially in the focal zone of the acoustic energy. A headspace control member may be positioned relative to the vessel to define a headspace in the vessel near the interface to be 20% or less of the sample volume. In some embodiments, the headspace may be 10% or less of the sample volume, e.g., as low as 0% of the sample volume where the headspace control member is located in contact with the interface or in the sample.

The headspace control member may be adjustably positionable in the vessel at or near the interface between the sample and the gas, e.g., have a distal end that can be adjusted in position relative to the interface to accommodate different or changing sample volumes. In some embodiments, the headspace control member may include a valve, a gas permeable membrane, a porous material, a filter, sponge, and/or an orifice, for allowing gas to pass through at least a portion of the headspace control member. Such arrangements may, in addition to other features, permit a pressure local to the sample in the vessel to equalize with an ambient pressure outside of the vessel. In some embodiments, the headspace control member may present a rigid surface to the interface and/or sample, e.g., to reflect acoustic energy and allow for higher acoustic input energies than would otherwise be possible. In some cases, the headspace control member may cause increased turbulence in the sample than would otherwise be present, which may allow for more rapid heat transfer (e.g., dissipation) and more thorough processing of the sample. In some cases, a rigid surface presented by the headspace control member may improve processing times, e.g., make processing up to 10 times faster than otherwise identical processing conditions that lack a rigid surface presented by a headspace control member.

The acoustic energy may be arranged in any suitable way, e.g., be sufficient to cause at least one of lysing, extraction, permeabilizing, stirring, catalyzing, degrading, fluidization, heating, particle breakdown, DNA shearing, or disruption of molecular bonds in the sample. In some embodiments, the acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel.

In another aspect of the invention, an acoustic treatment device includes a vessel having a total volume and arranged to hold a sample, and a sample including a liquid in the vessel, where the sample has a sample volume that is less than the total volume and defines an interface between the sample and a gas. An acoustic energy source may provide acoustic energy, having a focal zone, to the sample while the sample is in the vessel and is separated from the acoustic energy source, and a vessel holder may support the vessel at a location at least partially in the focal zone of the acoustic energy. A headspace control member may be adjustably positionable in vessel to define a volume of a headspace near the interface. For example, the headspace control member may include a cap arranged to engage with an opening of the vessel. The cap may be engaged with the vessel so that a lower or distal end of the cap may define a headspace at the interface between the sample and air in the vessel. In another embodiment, the headspace control member may include a porous member, or an impermeable member, positionable at or near the interface to define the volume of the headspace. In some arrangements, the headspace control member may float on the sample to define a headspace, e.g., to be 0% of the sample volume. The headspace control member may include a metal or ceramic element at or near the interface that is arranged to reflect acoustic energy. In one embodiment, the metal or ceramic element may include a plate having a thickness of about 0.5 to 1 mm.

In another aspect of the invention, a method for processing a sample includes providing a sample in a vessel, defining a headspace in the vessel at an interface between the sample and a gas, the headspace having a volume that is 20% or less than the sample volume, and subjecting the sample to acoustic energy sufficient to cause mixing of the sample. The acoustic energy may define a focal zone that at least partially overlaps the sample and is sufficient to cause at least one of lysing, extraction, permeabilizing, stirring, catalyzing, degrading, fluidization, heating, particle breakdown, or disruption of molecular bonds in the sample. The acoustic energy may have a frequency of between about 100 kilohertz and about 100 megahertz and have a focal zone with a width of less than about 2 centimeters. The acoustic energy may originate from an acoustic energy source spaced from and exterior to the vessel so that at least a portion of the acoustic energy propagates exterior to the vessel.

In some embodiments, the sample may include DNA fragments, and the acoustic energy may be sufficient to cause DNA shearing. The headspace may be defined by positioning a cap into engagement with an opening of the vessel such that a portion of the cap defines the headspace, by positioning a porous or impermeable member at or near the interface to define the volume of the headspace, and/or in other ways. The headspace volume may be defined to be 20%, 10%, or less of the sample volume, e.g., 0% or less of the sample volume.

In another aspect of the invention, an acoustic treatment device includes a vessel having a total volume and arranged to hold a sample including a liquid having a sample volume that is less than the total volume. An interface may be defined between the sample and a gas, e.g., at a top surface of the sample. A headspace control member may be positionable in the vessel to define a volume of a headspace near the interface. In some embodiments, the headspace control member may include a rigid surface that is presented to the interface, e.g., a metal or ceramic element that is positionable adjacent the interface for reflecting acoustic energy. In some embodiments, the use of metal or ceramic is not necessarily required so long as the headspace control member presents a surface with a suitable hardness to reflect acoustic energy in a way similar to that provided by a metal or ceramic element. The vessel and headspace control member may be arranged for use with an acoustic energy source that provides acoustic energy to the sample while the sample is in the vessel at a focal zone of the acoustic energy and is separated from the acoustic energy source. In some embodiments, the metal or ceramic element includes a metal or ceramic plate having a thickness of about 0.5 to 1 mm. This arrangement may provide the metal or ceramic element with sufficient rigidity to reflect acoustic energy back toward the focal zone, allowing the device to improve the efficiency of acoustic treatment.

"Mixing" is used herein to refer to a variety of different levels of doing work on the sample or otherwise moving sample material without physically contacting the material, including lysing (such as cell lysis), extraction, permeabilizing, stirring, catalyzing, degrading, fluidization, heating, particle breakdown, DNA shearing, or disruption of molecular bonds in the sample. In some embodiments, the acoustic energy has a frequency of between about 100 kilohertz and about 100 megahertz and a focal zone with a width of less than about 2 centimeters that is applied to the sample.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Figure 1:
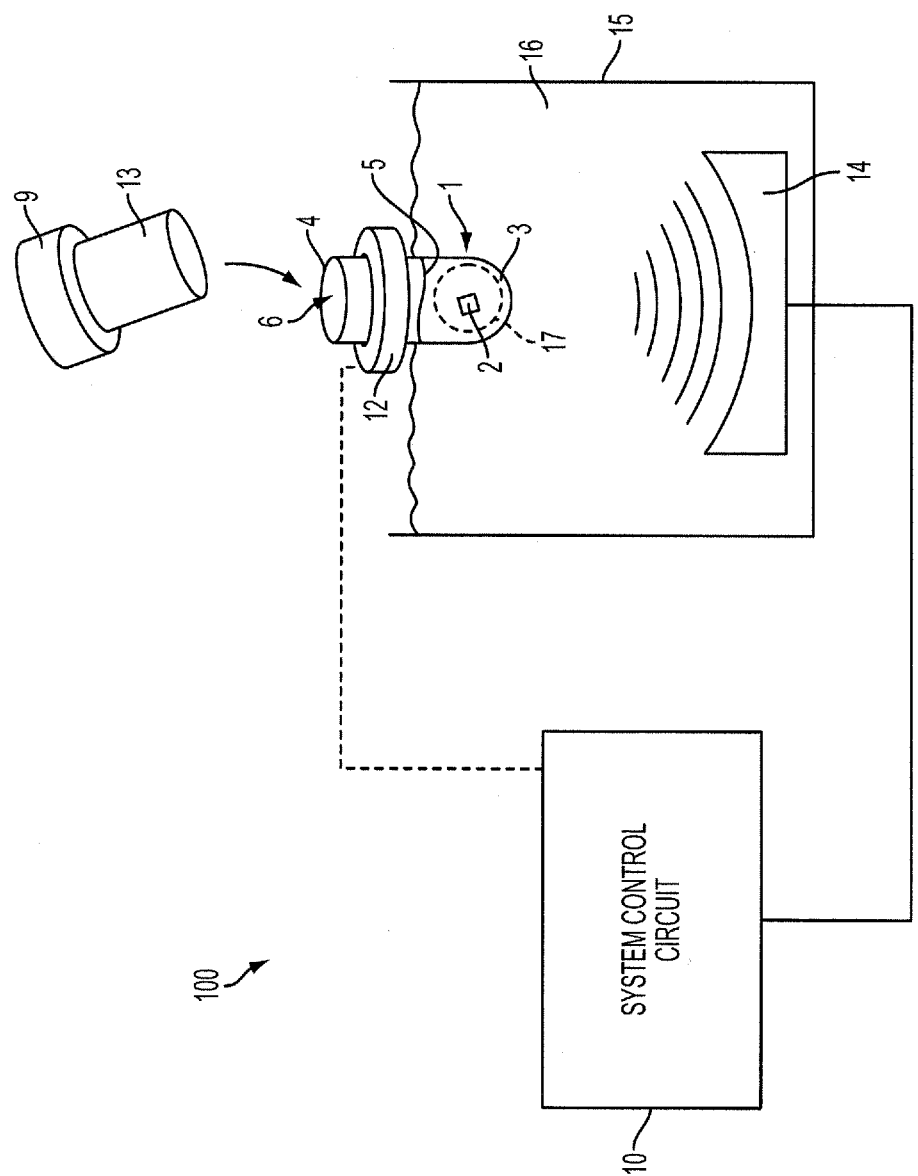
FIG. 1 shows a schematic block diagram of an acoustic treatment system that incorporates one or more aspects of the invention.

Aspects of the invention are not limited in application to the details of construction and the arrangement of components set forth in the following description or illustrated in the drawings. Other embodiments may be employed and aspects of the invention may be practiced or be carried out in various ways. Also, aspects of the invention may be used alone or in any suitable combination with each other. Thus, the phraseology and terminology used herein is for the purpose of description and should not be regarded as limiting.

As described above, acoustic treatment systems can be useful for the homogenization and disruption of biological tissues, cells and other sample material, with the end goal of recovering target molecules from the sample material, such as DNA, RNA, proteins, and the like. In addition, such systems may be used along with aspects of the invention for DNA shearing, e.g., to reduce the base pair length of DNA fragments from 1,000s or 10,000s of base pairs to lengths of 3 k base pairs or smaller. Examples of such acoustic treatment systems and control arrangements are described in U.S. Pat. Nos. 6,948,843 and 6,719,449, assigned to Covaris of Woburn, Mass.

Although acoustic-based sample disruption processes such as those performed using Covaris Adaptive Focused Acoustic systems are very efficient, they sometimes require that an operator define general treatment parameters before processing samples. For example, one common objective is to enable rapid and complete processing of a sample, e.g., to fully extract DNA, proteins or other materials in the sample, reduce heating of the sample, provide faster throughput when processing multiple samples, provide uniform acoustic treatment of a sample, and/or other features. Achieving this result often requires that the acoustic energy at the focal zone be essentially throttled down, e.g., by reduced intensity, duty cycle, and/or duration, to keep portions of a sample from splashing or otherwise moving out of the acoustic focal zone. For example, if a 1 gram muscle sample is loaded into a 10 ml tube with 2 ml of distilled water, there will be essentially 7 ml of headspace between the top surface of the sample (including the liquid and muscle material) and the top of the tube. If the acoustic energy applied to the sample is at a sufficiently high intensity, the sample/air interface in the tube may be readily broken. This may result in particles of the muscle material being splashed up and out of the focal zone, and/or result in air entering into the sample liquid, such as by dissolving or having bubbles trapped, at least temporarily, in the liquid. Particles that are ejected from the sample may adhere to the interior wall of the tube relatively far removed from the focal zone, possibly even as far away as a cap on the tube. A sample particle which is adhered to the tube wall or cap likely will not be homogenized or otherwise acoustically treated and the resultant homogenate may be incomplete and variable. To prevent this problem, what is typically done is to reduce the acoustic dose so the sample material is not ejected from the acoustic focal zone, and instead spends as much time as possible in the acoustic focal zone during a process.

In accordance with one aspect of the invention, a retention time of a sample in an acoustic focal zone may be increased, e.g., by minimizing the gaseous headspace size in a processing vessel and/or controlling interaction between the sample and acoustic energy, thereby enabling higher acoustic doses to be delivered to the sample. As a result, sample processing time may be reduced, improving processing efficiency and target recovery.

In another aspect of the invention, an efficiency of use of acoustic energy in a sample may be enhanced, e.g., by reducing an amount of gas that is entrained in the sample. In some embodiments, gas entrainment in a sample may be reduced by reducing or otherwise controlling a size of the headspace adjacent the sample. By reducing the volume and/or surface area of a headspace presented to a sample, an amount of gas available for entrainment into the sample can be reduced, or a rate at which the gas can be entrained may be reduced. This can help reduce bubble formation in the sample during acoustic treatment and/or interference of gas with cavitation bubble collapse, helping to increase an amount of acoustic energy that is used for treating the sample rather than being reflected out of the sample vessel or absorbed by increased cavitation bubble pressure.

In another aspect of the invention, a processing volume or volume within which all or a portion of a sample is located for acoustic treatment, may be controlled in a vessel. For example, the gaseous headspace in a vessel may be reduced by positioning a wall, stop or other headspace control member in the vessel so that the headspace control member is located at or desirably near (e.g., above or below) a top surface of a sample in the vessel. The sample may be liquid, solid, a mixture of solid material in a liquid, or any other suitable arrangement. The vessel may take any suitable form as discussed above, such as a tube, well in a microtiter plate, a cube-shaped vessel, etc. In one embodiment, the headspace control member may be suitably positioned with respect to the sample to reduce headspace without pressurizing the sample or other environment in the vessel. For example, the headspace control member may allow pressure in the vessel to equilibrate with an atmospheric or ambient pressure outside the vessel. In one aspect of the invention, a ratio of fluidic sample to headspace (e.g., gaseous space in the vessel between the headspace control member and the sample) may be 5:1, 10:1, or greater. That is, a volume of the headspace may be 20% or less of the sample volume.

In one illustrative embodiment, a headspace control member may include a check-valve, a gas permeable membrane, filter, porous material, or orifice. For example, if the vessel in which a sample is placed has the shape of a tube, the headspace control member may take the form of a plunger-like element that is inserted into the tube and suitably positioned in the tube so that the distal end of the plunger-like element is located at or near a top surface of the sample in the tube. A check-valve, gas permeable membrane, filter, orifice, bi-directional valve or other suitable component of the headspace control member may allow gas to pass by the member during insertion into and/or removal from the tube.

In another aspect of the invention, a headspace control member may be arranged to present a rigid surface to the sample to reflect acoustic energy back toward the sample and/or a focal zone of the acoustic energy. In some arrangements, the rigid, acoustic energy reflecting surface may significantly improve the efficiency of acoustic processing. For example, it has been surprisingly found that a metal plate located at or near a sample interface may reduce a processing time by a factor of up to 10 (i.e., processing can be completed up to 10 times faster than a processing arrangement that is otherwise identical but does not include a rigid element presented to the sample). The rigid surface may be provided on a side of the sample that is opposite the acoustic source, e.g., so that acoustic energy is reflected by the rigid surface back toward the sample and the acoustic source.

FIG. 1 shows a schematic block diagram of an acoustic treatment system 100 that incorporates one or more aspects of the invention, including an energy director that is associated with a sample. It should be understood that although embodiments described herein may include most or all aspects of the invention, aspects of the invention may be used alone or in any suitable combination with other aspects of the invention. In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 4. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass tube, a plastic container, a well in a microtiter plate, a vial, or other, and may be supported at a location by a vessel holder 12. In this embodiment, the vessel 4 is a standard rimless 13×100 mm borosilicate glass test tube, but it should be understood that the vessel 4 may have any suitable shape, size, material, or other feature. For example, the vessel 4 may be a cylindrical tube with a flat bottom and a threaded top end to receive a cap 9, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 4. In embodiments where the medium 16 includes a solid or semi-solid, a container 15 need not be provided or a portion of the medium 16 itself may function as a container 15, e.g., to hold a liquid or gas portion of the medium 16. For example, in one embodiment, the transducer 14 may be attached to a solid coupling medium 16 (such as a silica material), which is also attached to a vessel holder 12, which may be formed, at least in part, by an opening or other feature of the medium 16. Thus, the transducer 14, medium 16 and holder 12 may be formed as a single integrated part, if desired. In some embodiments, the acoustic field may be controlled, the acoustic transducer 14 may be moved, and/or the vessel 4 may be moved (e.g., by way of moving a holder 12, such as a rack, tray, platform, etc., that supports the vessel 4) so that the sample is positioned in a desired location relative to the focal zone 17. In addition, or alternately, the transducer 14 may form the focal zone 17 so that the focal zone 17 is suitably positioned relative to the sample 1 or vessel 4.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. As discussed in more detail below, the system control circuit 10 may control various other acoustic treatment system 100 functions, such as positioning of the vessel 4 and/or acoustic transducer 14 (a dashed line linking the control circuit 10 to the holder 12 schematically represents an optional positioning system, e.g., including a robot, gantry, screw drive, or other arrangement to move the holder 12), receiving operator input (such as commands for system operation), outputting information (e.g., to a visible display screen, indicator lights, sample treatment status information in electronic data form, and so on), and others.

In this illustrative embodiment, the sample 1 includes a solid material 2 and a liquid 3, e.g., 100 milligrams of a biological sample material in 1 milliliter of distilled water. Of course, those of skill in the art will appreciate that the sample 1 is not limited to a solid material 2 in a liquid 3, as the sample 1 may take any suitable form, such as a liquid only form, a solid only form, a mixture of liquid and solid as in this embodiment, a gel, a semi-solid, a gas, and/or combinations thereof.

An interface 5 separates the sample 1 from the headspace 6, which is shown to be a gaseous region immediately above the sample 1. For some power levels at the focal zone 17 and/or sample types or arrangements, acoustic energy suitable to cause mixing, e.g., lysing, extraction, permeabilizing, catalyzing, degrading, fluidization, heating, particle breakdown, shearing and/or disruption of molecular bonds in the sample 1, may also cause portions of the sample 1 (including solid material 2 and/or liquid material 3 of the sample 1) to be splashed or otherwise ejected from the interface 5. In some cases, the ejected sample 1 may return to the main volume of sample 1, but in other cases, the ejected sample 1 may adhere to the vessel 4 above the interface 5 or otherwise fail to return to the main sample 1. In either case, the ejected sample 1 may spend a reduced amount of time in the focal zone 17.

In addition, or alternatively, acoustic energy may cause gas in the headspace 6 to be entrained into the sample 1, such as by dissolving a portion of the gas in the headspace 6 and/or by capturing bubbles of headspace gas in the sample due to motion of the liquid at the interface 5. As discussed above, gas in the sample 1 may interfere with acoustic energy, such as by gas bubbles at or near the focal zone 17 reflecting acoustic energy away from the sample 1 and/or by dissolved gas increasing a pressure in cavitation bubbles created by acoustic energy, thereby decreasing the rate or force at which the cavitation bubbles collapse. The inventor believes that the collapse of cavitation bubbles transfers significant kinetic energy to sample materials, causing the materials to be lysed, sheared or otherwise mechanically operated on. By increasing a pressure in such bubbles, dissolved gas in the sample can reduce the energy released by cavitation bubble collapse, reducing an effectiveness of acoustic treatment.

Figure 2:
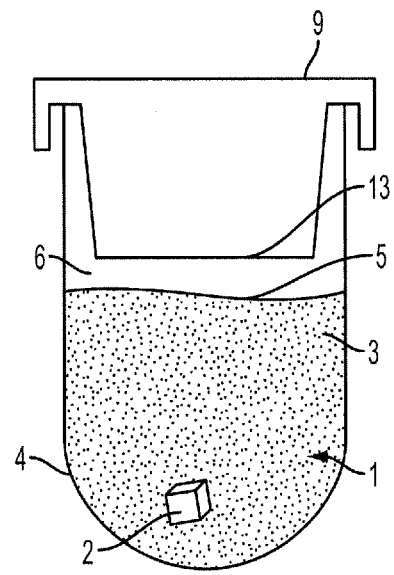
FIG. 2 is a section view of an embodiment of a sample in a vessel with a headspace control member associated with a cap.

In accordance with an aspect of the invention, a headspace at an interface of a sample can be controlled, e.g., in volume and/or surface area presented at the interface, to reduce an amount of gas available for entrainment in the sample. Headspace size (volume and/or surface area presented at the interface 5) can be controlled in a variety of different ways. For example, FIG. 2 shows a view of the vessel 4 in the FIG. 1 embodiment with a cap 9 engaged with the vessel 4 so as to position a headspace control member 13 near the interface 5. In this embodiment, the headspace control member 13 is attached to the cap 9 (e.g., formed as a unitary part with the cap 9), but other arrangements are possible as discussed more below. The headspace control member 13 may reduce a volume of the headspace 6 to be 20% or less than the volume of the sample. In some embodiments, the volume of the headspace 6 may be 10% or less than the volume of the sample 1, even as little as 0% of the sample volume where the headspace control member 13 is in contact with the sample 1 at the interface 5.

Figure 3:
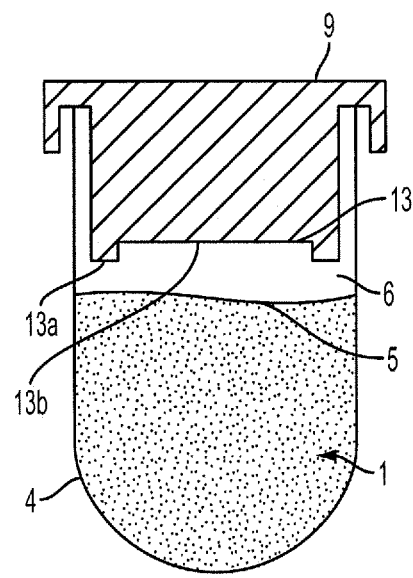
FIG. 3 is a section view of an embodiment of a vessel and headspace control member having a peripheral rim adjacent a sample interface.

While in this illustrative embodiment, the headspace control member 13 is arranged to have a frustoconical shape such that a lower portion of the headspace control member 13 has a smaller diameter than an upper portion, the headspace control member 13 could be arranged in other ways, e.g., to have a cylindrical shape, a pyramid shape, etc. FIG. 3 shows another illustrative embodiment of a headspace control member 13 that includes a lower portion having a peripheral rim 13a that depends below a center section 13b. Although in this embodiment the headspace control member 13 is arranged out of contact with the sample 1, the headspace control member 13 could be arranged to contact the sample 1, e.g., so that the rim 13a is located below the interface 5. Such an arrangement may not only reduce a volume of the headspace 6, but also reduce a surface area of the headspace 6 that is presented to the sample 1 at the interface 5. In another arrangement, the headspace control member 13 may be positioned relative to the interface 5 so that the center section 13b is also positioned below the interface 5, thereby further reducing the headspace size. The headspace control member 13 may be adjustably positioned in different ways, such as by having the headspace control member 13 engage the inner wall of the vessel 4 with a friction fit that allows the headspace control member 13 to be moved axially in the vessel 4, but holds the headspace control member 13 in place when a moving force is released. In another embodiment, the headspace control member 13 may threadedly engage with the vessel 4 so that rotation of the headspace control member 13 relative to the vessel 4 positions the headspace control member 13 in a desired way relative to the interface 5. In another arrangement, the headspace control member 13 may threadedly engage with the cap 9 or another element to allow for position adjustment of the headspace control member 13. Of course, other position adjustment features and/or shapes for the headspace control member 13 other than that shown in FIG. 3 are possible. As mentioned above, the headspace control member 13 may have a pyramid shape, e.g., so that a point of the pyramid may be positioned below the interface 5. Other shapes are possible, such as a cylindrical shape, a bullet shape, etc.

Figure 4:
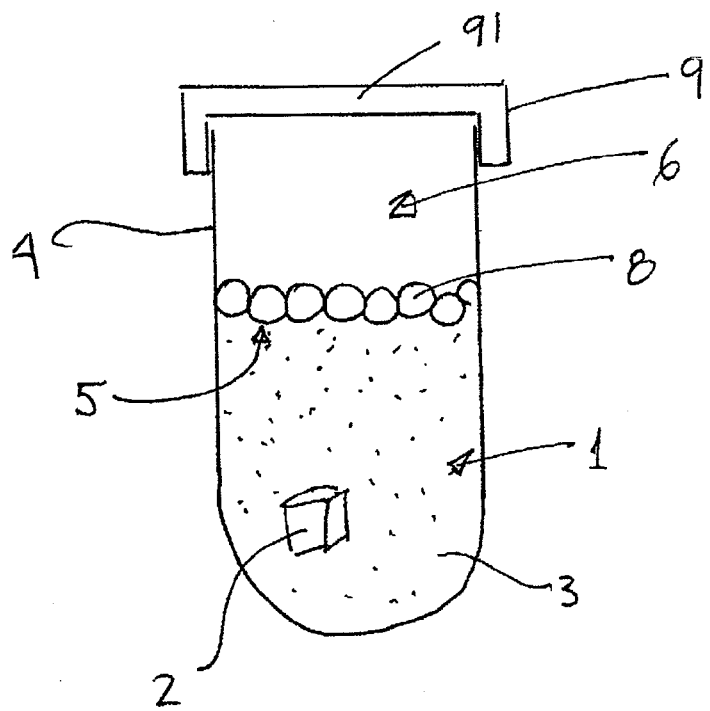
FIG. 4 is a section view of an embodiment of a vessel and headspace control member in the form of one or more beads.

In some arrangements, a position of the headspace control member 13 relative to the interface 5 may be defined by interaction of the headspace control member 13 with the interface 5. For example, FIG. 4 shows an embodiment in which bead-shaped elements are used as a headspace control member 13. In this example, beads may be buoyant so as to position themselves at the interface 5 and to help control a size of the headspace 6 in relation to the sample 1. A physical separation between the headspace 6 and the sample 1 may be maintained by the beads, even during a high power focused acoustic dose that might otherwise cause sample ejection. In some embodiments, after an acoustic process is complete, the sample 1 may be aspirated by a pipette that pushes the beads to the side as the pipette tip opening is lowered below the surface of the sample fluid 3, avoiding any need to remove the headspace control member 13 from the vessel 4. Other materials and configurations may be appropriately used for the headspace control member 13 that interacts with the interface 5, such as a plug (e.g., made of Porex), a disc, wafer, or the like that is arranged to float or otherwise position itself at the interface 5. Such an arrangement may avoid any need to position the headspace control member 13 relative to the interface 5 since the headspace control member 13 may be self-positioning.

Although in the embodiment shown in FIG. 4 the beads are buoyant in the sample liquid 3 so that the beads float at the interface 5, the beads or other headspace control member 13 may be arranged to position itself at the interface 5 in other ways. For example, the beads may have physical properties such that when the sample 1 is under a focused acoustic energy dose, the beads are elevated upward or otherwise moved to or near the interface 5, e.g., by acoustic streaming. In one arrangement, the beads may be made of a polymer material (e.g., polypropylene, Bangs Labs) and may be of different sizes. The vessel 4 in this embodiment may be annealed borosilicate glass (e.g., 6×32 mm) and include a septa 91 (e.g., having a split septum or other piercable portion) as part of the cap 9, e.g., to admit a pipette needle into the vessel 4.

Figure 5:
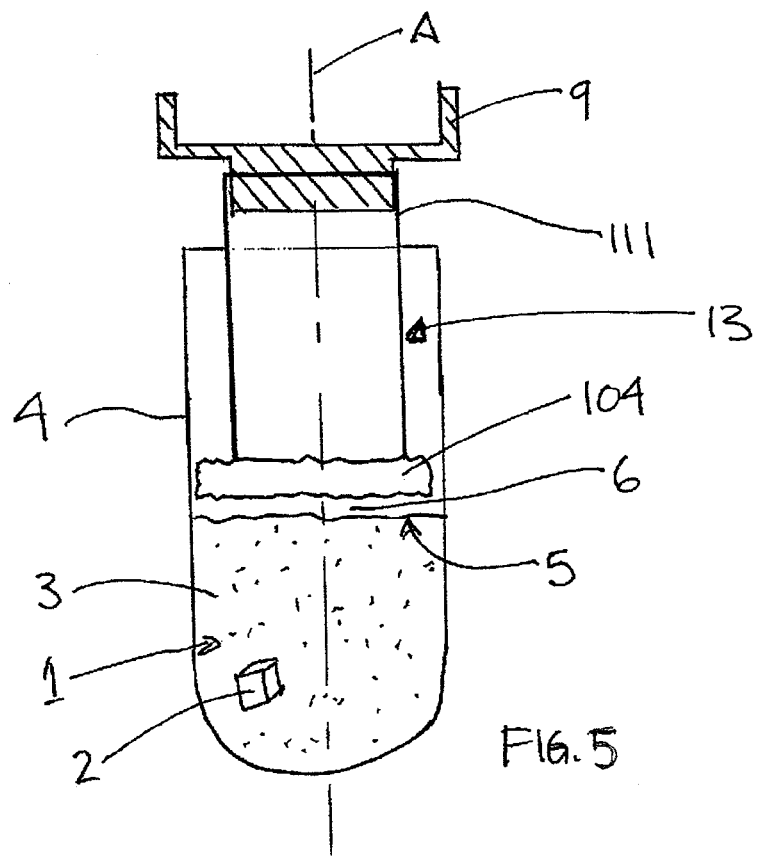
FIG. 5 is a section view of an embodiment of a vessel and headspace control member including a porous element.

FIG. 5 shows another illustrative embodiment of a headspace control member 13. In this arrangement, the headspace control member 13 includes a piston-like arrangement suitable for insertion into the open end of the vessel 4 and positioning of the distal end of the headspace control member 13 near the sample 1. As shown, the headspace control member 13 may include a number of features, such as a cylindrical tube 111 that carries an element 104 arranged to allow the member 13 to be moved axially along a longitudinal axis A in the vessel 4. In some cases, characteristics of a portion of the headspace control member 13 that faces the sample 1 may affect acoustic processing results, e.g., a portion of the volume control element 13 may function to enhance an affect of acoustic energy on the sample 1. Such characteristics of the volume control element 13 that may affect sample processing include, for example, choice of material, nominal pore size, and hydrophobicity. In this embodiment, the element 104 includes a piece of porous, hydrophobic material (e.g., a scaffold or matrix-type material) that may function, at least in part, to not only control a headspace size, but also enhance an effect of acoustic energy on the sample 1. This arrangement may be useful, e.g., in DNA shearing applications. In accordance with another aspect of the invention, the porous structure of the element 104 may also permit pressure in the vessel 4 at the sample 1 to equilibrate with pressure above the element 104. Further, if the element 104 is positioned below the interface 5, the element 104 may act as a type of filter, allowing portions of the sample 1 to pass, while maintaining larger solid material 2 below the element 104.

The element 104 and/or the tube 111 may be arranged so that the headspace control member 13 is self-positioning at the interface 5, e.g., the element 104 and/or the tube 111 may be buoyant and float in or on the sample 1. In another arrangement, the element 104 and/or the tube 111 may be arranged to engage with the vessel 4 or other component to position the headspace control member 13 suitably with respect to the interface 5, e.g., by an interference or friction fit, threaded engagement, contact with a stop or other feature in the vessel 4, and so on.

The embodiment shown in FIG. 5 also includes a cap 9 that may be used to close the proximal end of the tube 111 of the headspace control member 13. By capping the proximal end of the headspace control member 13, an operator may be able to prevent flow through or otherwise past the element 104 and/or prevent contamination of the sample 1 by the outside environment. Although not required, the cap 9 may be arranged as shown in FIG. 5 so as to allow capping of the vessel 4, if desired. In this illustrative embodiment, one end of the cap 9 may engage with the tube 111 of the headspace control member 13 (shown in FIG. 5), whereas the opposite end of the cap 9 is enlarged so as to allow the cap 9 to be reversed from the position shown in FIG. 5 and placed on the end of the vessel 4.

In some embodiments, the processing volume (a volume in the vessel 4 that is acoustically treated) may include portions of the headspace control member 13. For example, a portion of the sample (liquid and/or solid) may pass into or through a portion of an element 104 (such as the porous, hydrophobic element described above) and still be subjected to acoustic energy. Although the processing volume may extend through a portion of the headspace control member, the headspace control member may still serve to substantially confine the processing volume so that the sample may be suitably exposed to acoustic energy. As a result, the processing volume may be a volume defined by the headspace control member itself; for example, a portion of a filter that traps sample particles for acoustic processing, in addition to, or in place of a portion of the vessel. Once the processing volume is defined, the portion of the sample in the processing volume may be subjected to acoustic energy sufficient for gentle movement, lysing, extraction, permeabilizing, stirring, catalyzing, degrading, fluidization, heating, particle breakdown, disruption of molecular bonds, or any other appropriate process, in the sample.

In another illustrative embodiment, a portion of the headspace control member director may be arranged to enhance the fragmentation of DNA materials and/or otherwise influence the interaction between acoustic energy and the sample. In one specific example, a porous, generally hydrophobic plug of a polymer material (such as polypropylene or Porex material) may be positioned at or below the interface 5 in a 50-100 microliter vessel containing a sample 1 with DNA material. The plug may be attached to a cap 9, such as that shown in FIG. 2, and depend downwardly from the cap so that at least a portion of the plug is located at or below the interface 5. In one embodiment, the cap 9 is made from a solid piece of plug material and is arranged to not only cover the opening of the vessel 4, but also have a lower portion extend to the interface 5. The plug may have randomly or otherwise arranged pores (i.e., voids) that are exposed to the sample to assist in enhancing the shearing operation. The pores may range in size, for example, from 10-200 microns depending on the particular application. In one embodiment, the plug has pore sizes of about 100 microns with the pores randomly arranged. In this example, the starting DNA material may include DNA segments having a size of about 48.5 kbp. Acoustic treatment may be provided using a Covaris S2 AFA machine employing a 10% duty cycle, a 0.5 intensity level and 200 cycles per burst for approximately 4-8 minutes. After treatment, the majority (if not all) of the DNA fragments in the sample 1 are reduced in size to about 3 kbp. A fairly narrow range of final DNA fragment sizes may be produced, e.g., most of the DNA fragments may fall in a size range of about 1.5 kbp to about 5 kbp, and the range of DNA fragment sizes produced may be adjusted by adjusting characteristics of the energy director plug, including the material type, nominal pore size of the material and the hydrophobicity.

In contrast to the FIG. 5 embodiment described above, the element 104 may have a more impermeable arrangement, e.g., be formed of a flexible rubber or other suitable elastomer having a portion sized to be inserted in the distal end of the tube 111 so as to frictionally engage the element 104 with the tube 111. The element 104 may also include an annular sealing portion that contacts the inner wall of the vessel 4 and prevents the passage of liquid and/or gas at the contact point between the seal member 104 and the vessel 4, for example, similar to the manner in which a syringe plunger seals with a corresponding syringe barrel. In another illustrative embodiment, the headspace control member 13 may have the element 104 arranged so that a relatively small amount of liquid and/or gas may pass, for example, the annular seal member 104 may have a small cut or notch that prevents formation of a complete seal with the vessel wall. In another illustrative embodiment, the member 13 may have a one-way valve, for example, that allows gas and/or liquid to pass as the member 13 is inserted into or withdrawn from the vessel 4. In another embodiment, the member 13 may include a bi-directional valve that allows gas and/or liquid to pass as the member 13 is inserted into and withdrawn from the vessel 4. In various embodiments, the member 13 may include an orifice, serpentine passage, membrane or other structure that allows passage of gas and/or liquid in a controlled manner, yet prevents substantial portions of the sample material from exiting a desired area in the vessel 4. The headspace control member 13 may be made of any suitable material or combination of materials, such as plastic, rubber, metal, glass, or the like. These materials may be selected based on any suitable criteria, such as chemical resistance, resiliency, stiffness, heat resistance, acoustic properties, etc. In one embodiment, the member 13 includes a PTFE material that is presented on a side near the sample, for example, to help prevent undesired adherence of the sample material to the member 13. In another embodiment, the element 104 having a flexible rubber portion may also include a porous portion like that described above, which may function as a type of filter.

Figure 6:
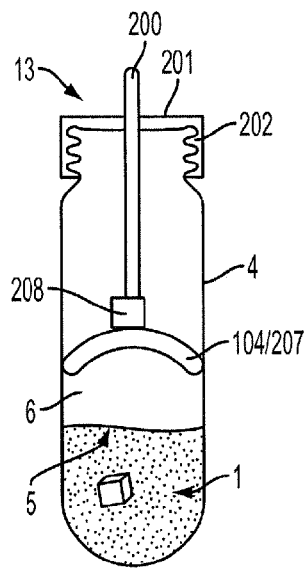
FIG. 6 is a section view of yet another embodiment of a sample in a vessel with a headspace control member in accordance with aspects of the invention.

FIG. 6 shows a illustrative embodiment of a sample vessel and headspace control member that includes a generally impermeable material. In this embodiment, a cylindrical vessel 4 (e.g., 13×65 mm borosilicate glass), which includes a matched screw-threaded cap 202 and septa 201, is shown with a headspace control member 13 in the form of an adjustable piston assembly, including a rod 200, a couplant 208 to affix the tip with the rod and an element 104 in the form of a piston tip 207. The rod 200 may be formed by any suitable manner, such as injection molding. Any suitable couplant 208 may be used, such as a crimped metal or extruded plastic ring. The piston tip 207 may be formed from any appropriate material, such as silicone, rubber, other plastic, or the like. The rod 200 is inserted through a slit or other opening in the septa 201, allowing the headspace control member 13 to be moved vertically relative to the septa 201. In this embodiment, the piston tip 207 is of greater diameter than the internal diameter of the cylindrical vessel 4, allowing for an interference fit between the piston tip 207 and the vessel 4.

For example, an interference fit shown in FIG. 6 may be formed by the piston tip 207 having a 1.0 millimeter greater diameter than the internal diameter of 10 millimeters of the vessel 4. The degree of interference may be dependent on several factors, including the durometer, thickness, and/or material of the piston tip 207. In one embodiment, the tip 207 is preferably made of a polymeric material. The interference fit may allow a piston tip 207 to be both inserted into and removed from a vessel which has a constricting neck. During sample loading, the flexible tip 207 may take a convex shape on its bottom surface relative to the sample at or near the interface 5 and allow pressure in the vessel 4 to be vented close to or at the ambient atmospheric pressure. Venting may occur, for example, in a space between the piston tip 207 and the vessel wall. If the piston rod 200 is pulled in the opposite direction away from the sample a slight distance, the piston tip 207 may invert, causing the convex shape assumed during insertion to become concave, as shown in FIG. 6. A concave surface of the piston tip 207 facing the sample at or near the interface 5 may help prevent sample material from being splashed upward out of the focal zone during a high power dose and aid the return of any ejected sample material back to the main sample. In addition, a concave shape of the piston tip 207 may minimize sharp edges (as may occur with a convex shape) to aid in the return of the sample to the main sample.

Figure 7:
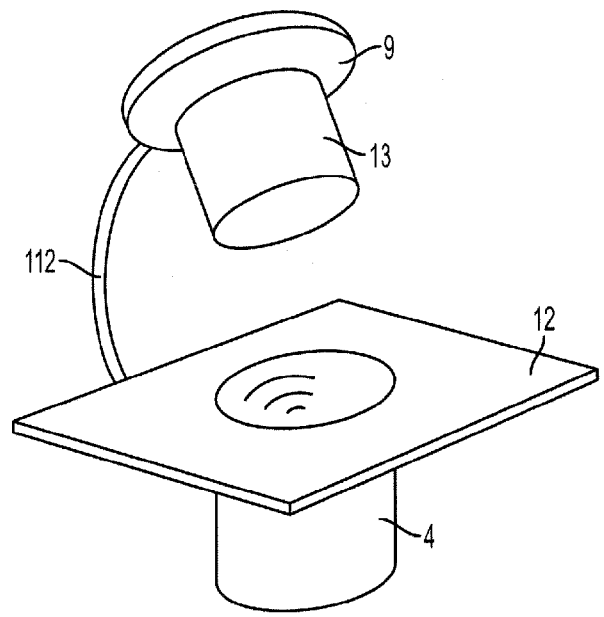
FIG. 7 is a perspective view of a further embodiment of a vessel and a headspace control member in accordance with aspects of the invention.

It should be understood that in one embodiment, the vessel 4, vessel holder 12, and/or headspace control member 13 may be separately formed parts that are later associated together, whereas in another embodiment, the vessel 4, vessel holder 12, and/or headspace control member 13 may be unitarily formed, e.g., molded together as a single piece. For example, FIG. 7 shows another illustrative embodiment of a sample vessel in which multiple components are formed as a single piece. In this embodiment, the vessel 4 and the holder 12 are molded as a single unitary piece with the vessel 4 depending from the holder 12. Although in this embodiment, the vessel 4 has a cylindrical shape and the holder 12 has a rectangular shape, it should be understood that the vessel 4 and the holder 12 may take any suitable configuration. Thus, the vessel 4 may define a cylindrical, conical, frustoconical, cubic or other box-like, spherical, mushroom-like or other suitably shaped volume for receiving the sample. The holder 12 may have an elliptical, circular, rectangular, triangular, or other shape, at least as viewed from the top. In a 3-dimensional sense, the holder 12 may take a conical, cylindrical, frustoconical, cubic or any other shape or combination of shapes. Of course, the holder 12 or the vessel 4 may have an irregular shape of any suitable kind.

Also in this embodiment, the headspace control member 13 is attached to a cap 9, with a cylindrical portion depending from a circular cap 9, e.g., similar to that shown in FIG. 2. As in the embodiments described above, the member 13 may include a valve structure, filter, porous material, orifice, sponge, or other arrangement to allow selective passage of gas. In one embodiment, the cylindrical portion may have a slot, groove, flat or other feature on its sidewall that prevents the formation of a complete seal with the vessel 4, thereby allowing gas to pass. In another embodiment, the cylindrical portion may be sized smaller than the vessel inner wall to prevent a complete seal from being formed between the member 13 and the vessel 4. Although in this embodiment the member 13 may be separate from the vessel 4 and holder 12, it is possible to have the member 13 attached to the vessel 4 or holder 12, for example, by a hinge, tether 112, or other feature. For example, it is possible to mold the vessel 4, holder 12, and the member 13 as a single unitary member with a tether 112 connecting the member 13 to the holder 12 as shown in FIG. 7. The headspace control member 13 may be arranged to be adjustably positioned in the vessel 4, e.g., to control a size of a headspace 6, in any suitable way, such as by interference fit of the cap 9 with the vessel 4, threaded engagement of the headspace control member 13 with the cap 9, and so on.

Figure 8:
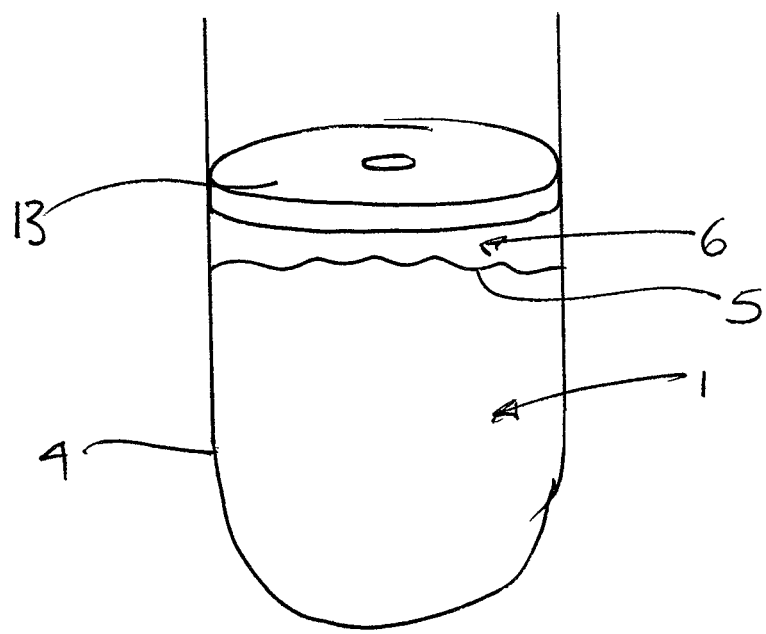
FIG. 8 is a side view of an embodiment of a vessel and headspace control member in the form of a washer element.

Although in many of the embodiments above, the headspace control member 13 is attached to a cap 9 or includes a tube 111, rod 200, or similar element, the headspace control member 13 need not include any such component. Instead, the headspace control member 13 may include an element, such as a washer-shaped component, that is positioned at or near an interface 5 of a sample. For example, as shown in FIG. 8, the headspace control member 13 may be provided by a washer element that is placed into the vessel 4, molded with or otherwise formed as part of the vessel 4, floated on the sample 1 or otherwise provided. In one embodiment, an O-ring or similar element may be provided in the vessel so that the O-ring frictionally engages the inner wall of the vessel and is suitably located at or near the interface 5. The washer element may be placed on the O-ring and supported in the vessel relative to the interface 5 by the O-ring. The washer element may include one or more holes, e.g., to provide access to the sample yet still function to control a size of the headspace 6 in a suitable way. Thus, the headspace control member 13 need not be separable from the vessel 4, but instead may be attached to the vessel 4 or otherwise provided as part of the vessel.

In another aspect of the invention, the headspace control member may include a rigid surface that is presented to the sample interface so as to reflect acoustic energy back toward the sample. As is explained and detailed more in Examples 4 and 5 below, it has been surprisingly found that a rigid surface, such as that provided by a metal or ceramic plate having a thickness of about 1 mm, provided at or near the interface of a sample can significantly enhance the efficiency of acoustic treatment.

In some cases, the rigid surface may be provided on a side of the sample opposite the acoustic source, e.g., so that the rigid surface reflects acoustic energy back toward the sample and the acoustic source. By providing a hard surface at such a location more efficient processing and more effective heat transfer from the vessel may be provided. For example, by having a stainless steel boundary surface at the distal, internal wall of a vessel (e.g., at the interface 5 of a sample that is on a side of the sample opposite an acoustic source) may result in micronization processes to be run 2 to 3 times faster than otherwise identical treatment arrangements that instead employ a plastic, polymeric distal, internal wall (e.g., a plastic surface at or near the interface 5). The hard or rigid surface is thought to absorb less of the energy involved in acoustic streaming, which at higher energies imparts more bulk turbulence in the sample. More turbulence may improve thermal energy dissipation and more thorough processing (e.g., 99% vs. 75% per unit time). In addition, the stainless steel or other rigid surface may enable higher input energies to be applied to the sample, e.g., more than twice the energy may be applied to a sample, such as 250 watts versus 100 watts for a treatment arrangement that uses a polymeric material at or near the interface. The net result in some cases is faster processing, higher energy applied to the sample, and more turbulence that can increase processing rates to be up to 10 times faster.

Embodiments that incorporate a hard or rigid surface located at or near an interface for reflecting acoustic energy (e.g., back to a sample in a direction generally toward an acoustic source) may be arranged in a variety of different ways, such as those shown in FIGS. 1, 2, 3, 5, 6, 7, 8 and 9. For example, the arrangement shown in FIG. 2 or 3 may include a metal or ceramic plate that is attached to a lower end of the cap 9 so that the metal or ceramic plate is located at or near the interface 5 when the cap 9 is engaged with the vessel 4. As another example, the arrangement in FIG. 8 may have the washer element made of a suitably size (e.g., thickness and diameter) metal or ceramic plate with or without a central hole. The metal or ceramic plate may have a size that is the same or approximately the same as the cross section of the vessel 4, and may have a thickness suitable to reflect acoustic energy, such as 0.5 more. Suitable metal materials include stainless steels and others.

In another aspect of the invention, a method for processing a sample includes providing a sample in a vessel, the vessel having a total volume, and the sample having a sample volume that is less than the total volume of the vessel. A processing volume may be defined in the vessel such that the processing volume is less than the total volume of the vessel and is a volume in which sample material to be subjected to acoustic energy is substantially confined. For example, if a 2 ml sample including liquid and solid material is placed in a 10 ml tube, a headspace control member may be placed in the tube so as to define a processing volume that is less than 10 ml in which the sample is largely confined to during acoustic processing. The processing volume may be larger than the sample volume, e.g., 3 ml, such that there is a headspace present in the processing volume, or may be less than the sample volume, e.g., 1 ml. If the processing volume is less than the sample volume, some portions of the sample, e.g., liquid portions, may be permitted to exit the processing volume (e.g., by passing through a filter or other porous portion of the headspace control member) while other portions of the sample (e.g., solid particles) may be kept in the processing volume. Once the processing volume is defined, the portion of the sample in the processing volume may be subjected to acoustic energy sufficient for gentle movement, lysing, extraction, permeabilizing, stirring, catalyzing, degrading, fluidization, heating, particle breakdown, disruption of molecular bonds, etc., in the sample. In one embodiment, the processing volume may be a volume defined by the headspace control member itself, e.g., a portion of a filter that traps sample particles for acoustic processing, in addition to, or in place of, a portion of the vessel. A volume of the headspace may be arranged to be 20% or less of the volume of the sample.

This aspect of the invention may provide advantages in some applications, such as when a relatively small amount of sample material is to be processed. That is, a small amount of sample material may in some cases require a relatively small processing volume be used during acoustic treatment, e.g., to ensure proper homogenization or other acoustic treatment. However, if a headspace control member is not used, providing a small volume for acoustic processing of the sample may require the use of a very small vessel. In reality, manually or otherwise placing a small sample in a small vessel may be difficult, resulting in portions of the sample being lost or damaged. In accordance with this aspect of the invention, a relatively large vessel may be used to receive the sample, but the actual volume of the vessel in which the sample is located during acoustic processing may be reduced to a small size through the use of a headspace control member. Thus, a relatively large vessel may be effectively converted to a small volume vessel for purposes of acoustic processing. Additionally, controlling interaction between a sample and acoustic energy directed to the sample may occur by minimizing the gaseous headspace above the sample in a processing vessel. As a result, a barrier may prevent sample material from traveling significantly from the main sample volume and/or may help reduce gas entrainment into the sample, and thus higher acoustic doses may be delivered to the sample. With higher acoustic doses, sample processing time may be reduced, further improving processing efficiency and target recovery.

Figure 9:
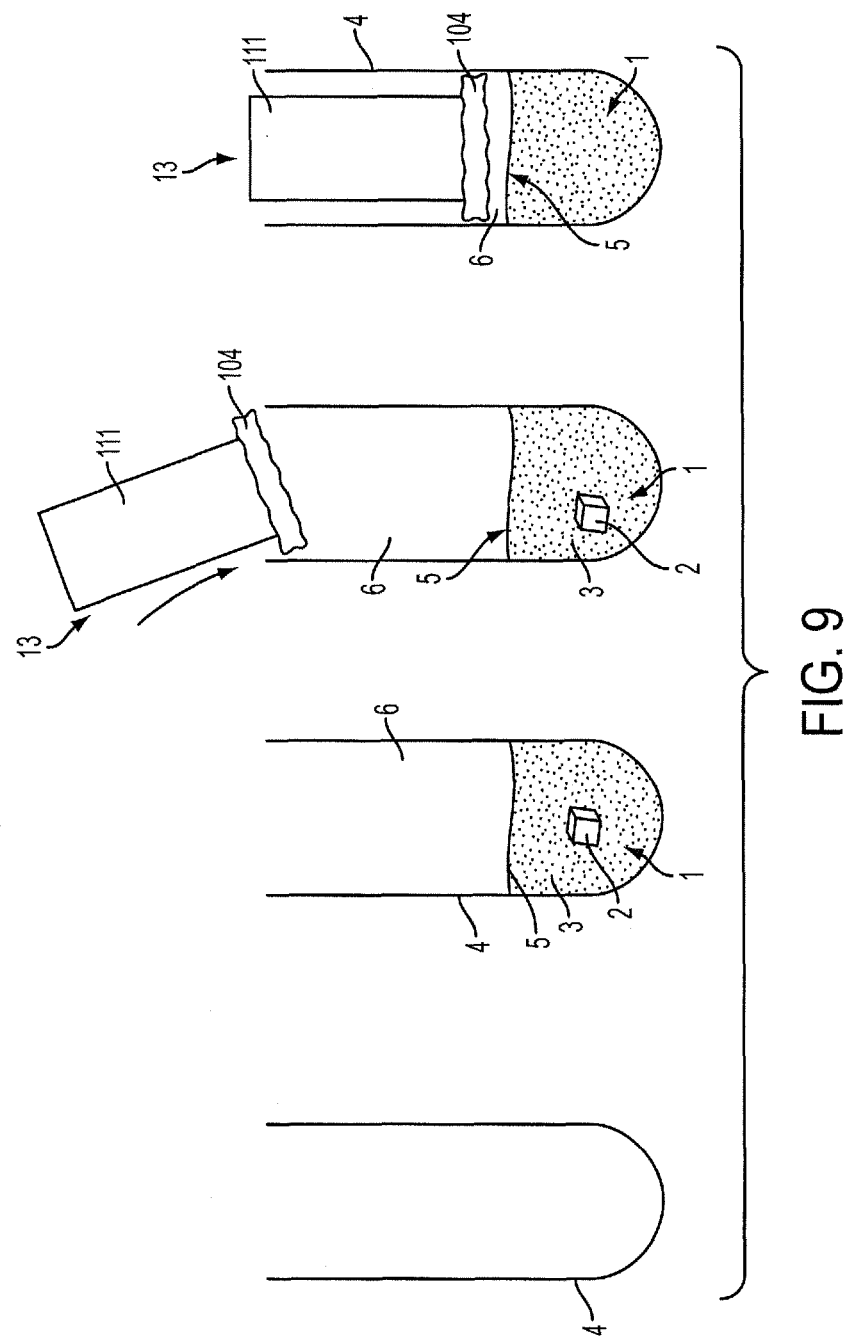
FIG. 9 shows steps in an illustrative method for providing a sample in a vessel with a headspace control member in accordance with aspects of the invention.

As shown in FIG. 9, when preparing a sample for processing by an acoustic processing device, a solid material 2 may be placed in the vessel 4 and liquid 3 or other material may be added to form the sample 1. Of course, placing a solid material 2 in the vessel 4, if performed at all, may occur subsequent to placing a liquid 3 in the vessel 4. As discussed above, the sample 1 may include one or more liquids, solids suspended or otherwise carried by a liquid, a gel, or any other suitable form. Regardless of the form of the sample 1, the sample may have an interface 5, which may be a gas/liquid interface, a gas/solid interface, or other suitable interface. To define the volume in which the sample 1 is to be processed, a headspace control member 13 may be placed into the vessel 4, for example, as depicted in FIG. 5, by inserting the distal end of the tube 111 with the element 104 into the interior of the vessel 4 until the element 104 is suitably positioned near the sample interface 5 (i.e., above, at or below the interface 5).

The headspace control member 13 may be positioned as desired, whether above the sample interface 5 as shown in FIG. 9, at the sample interface 5, or below the sample interface 5. In FIG. 9, no matter how large the headspace 6, being a gas-filled portion of the vessel adjacent the sample into which the sample may move, may be, the pressure Pi of headspace 6 may be allowed to equilibrate with the pressure Po of the ambient environment. As shown, during acoustic processing, the headspace 6 may be decreased so as to minimize significant travel of sample material from the interface 5 and/or to reduce gas entrainment. If the element 104 is positioned at or below the sample interface 5, the headspace 6 may be effectively reduced to zero. In such a case, the material in the sample sought to be acoustically processed may be confined by the member 13 and not allowed to pass the member 13 as it is inserted into the vessel 4.

In some embodiments, the vessel 4 may contain a sample 1 that includes liquid 2 that nearly fills the vessel 4 and a solid material 3 suspended throughout the liquid. If the headspace control member 13 is arranged like that in FIG. 5, the member 13 may serve to effectively filter the solid material 2 from the liquid 3 as the member 13 is advanced into the vessel 4 and allow liquid to pass and collect at the top of the vessel 4 while forcing the solid material 2 to collect near the bottom of the vessel 4. This may allow the solid material 2 to be confined to a smaller volume in the vessel, for example, near the bottom, and subjected to acoustic energy.

In another embodiment, the headspace control member 13 may function to collect material for acoustic processing. For example, solid particles in the sample may be trapped in the element 104 in the embodiment of FIG. 5, and the trapped particles may be subjected to acoustic energy while contained in the element 104. Acoustic processing may break the particles into smaller pieces, allowing the material to be dissolved or otherwise be released from the element 104.

In accordance with another aspect of the invention, a vessel may be associated with a holder that helps support the vessel during acoustic treatment. A holder 12 may take any suitable arrangement, such as a ring-shaped element 12 that is fixed relative to the vessel 4, as shown in FIG. 1. The holder 12 may be permanently fixed to the vessel 4, e.g., molded integrally with the vessel 4, attached to the vessel 4 by an adhesive, a fastener, welding, etc., or may be removably attached to the vessel. For example, in some embodiments, the vessel holder 12 may include a ring member like that shown in FIG. 1 and one or more O-rings (not shown) or other friction-enhancing elements that are positioned between the ring member and the vessel 4 to provide a tight friction fit between the vessel 4 and the holder 12. Such an arrangement may be useful when interchanging vessels 4 on a single holder 12 and/or adjusting the position of the vessel 4 relative to the holder 12.

Although a vessel holder 12 is not necessarily required, the vessel holder 12 may serve to interface with the acoustic processing device so that the vessel 4 and the sample in the vessel is positioned in a known location relative to an acoustic field, for example, at least partially within a focal zone of acoustic energy. Such an arrangement, coupled with the use of a headspace control member 13, may allow an operator to closely define the location in which the sample is positioned during acoustic processing.

Figure 10:
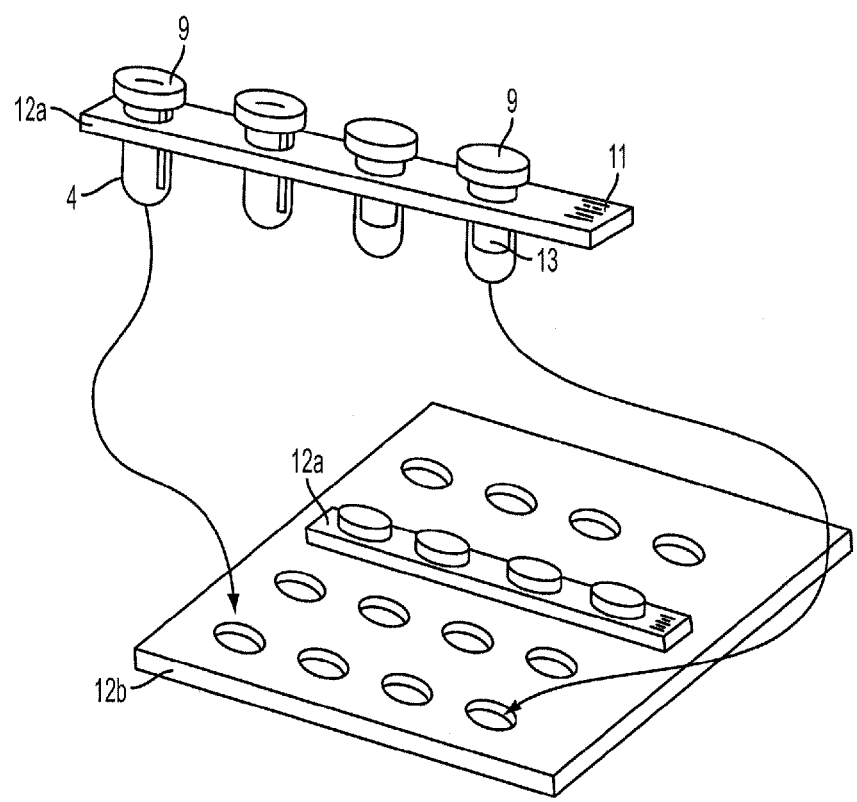
FIG. 10 shows an embodiment in which a holder includes a support that holds a subset of vessels and a rack arranged to receive a plurality of supports and associated vessels.

Although in the FIG. 1 embodiment the holder 12 is located near a middle of the vessel 4, the holder 12 may be positioned in any suitable manner relative to the vessel 4, such as near the bottom or top of the vessel, extending from one side of the vessel, and/or any other appropriate position. Also, the holder 12 is not limited to a device like that shown in FIG. 1, and instead may include a rack, slot, tray, gripper element, clamp, box or any other suitable arrangement for holding the vessel in a desired location. For example, FIG. 10 shows an arrangement in which the holder 12 includes one or more multi-vessel supports 12a and a rack 12b. Each support 12a may hold a plurality of vessels 4, e.g., in a linear array as shown. Although in this embodiment the support 12a is arranged to hold four vessels 4, any suitable number of vessels may be associated with a support 12a, such as eight tubes in a linear array. Each support 12a may include an identifier 11, such as a barcode, RFID chip, or other component that may be read so as to identify the support 12a and/or vessels 4 associated with the support 12a. The vessels 4 may be arranged in any desired way, such as having a cap 9 having a split septum (to allow aspiration/dispense of sample in the vessel 4 without removing the cap 9) as shown on the left end of the support 12a above the rack 12b, or a cap 9 with a headspace control member 13 that depends down into the vessel 4 to interact with the sample as shown on the right end of the support 12a. The vessels 4 may be held in place by an interference fit with holes formed in the support 12a, or may otherwise be associated with the support 12a. In this embodiment, the vessels 4 depend below the support 12a so that lower ends of the vessels 4 may be received in corresponding holes in the rack 12b. The rack 12b may have any suitable arrangement, but in this embodiment includes a plate with holes formed in an arrangement to receive multiple supports 12a and associated vessels 4. The rack 12b may make it easier to physically manipulate or otherwise handle multiple vessels 4, e.g., in an automated processing environment in which one or more robotic devices manipulate vessels for acoustic or other processing. The rack 12b may also include an identifier (not shown) so that the rack 12b and/or supports 12a on the rack 12b can be identified in a automated way, e.g., by a laser scanner, optical camera, RFID tag reader or other arrangement.

A few examples regarding use of a headspace control member arranged like that in FIG. 5 are described below.

Example One

Tissue samples, approximately 500 milligrams of frozen chicken breast tissue (solid piece), were stored at −70 degrees C. and inserted into a test tube vessel. 1.5 milliliters of distilled water (prechilled to <10 degrees C.) was added to the tube. A headspace control member 13 with a porous p-propylene material functioning as a vent or filter was inserted into the tube and the member 13 moved into position just above the fluid level leaving approximately 0.5 milliliters of gas/vapor headspace. The tube was inserted into a Covaris S2 system for 30 seconds at duty cycle 20%, intensity 10, and 200 cycles/burst. The member 13 kept the sample in the focal zone, eliminated the need for a degassing step, and accelerated homogenization of the tissue sample. Following homogenization, the member 13 was removed and the vessel with the sample was capped.

Example Two

As in Example one above, however, after the Covaris S2 acoustic process, 4 milliliters of MeOH was added to the headspace control member's 13 inner compartment (inside the cylindrical tube 111) and the member 13 was moved to enable the solvent to pass through the member 13 and into the homogenate. The homogenate plus MeOH was then treated for less than 10 seconds to mix and the member 13 was pressed to allow the extracted material to pass through the porous element 104, while leaving the particulate and material at the bottom of the vessel 4.

Example Three

Shearing of a 3 kb target fragment of DNA was performed using a Covaris S2 system for a single sample and a Covaris E210 system for multiple samples. A polypropylene tube was used as a vessel and was attached with a snap cap. The duty cycle used was 10% at an intensity of 0.1. There were 1,000 cycles per burst for a time period of 420 seconds. The temperature of the bath was 20 C. A frequency sweeping power mode was set under a continuous degassing mode. The volume of the vessel was 95 microliters, the buffer used being tris EDTA at pH 8.0 (no glycerol). A plug-type energy director was used. Less than 1.5 micrograms of DNA were used. The starting material including DNA fragments with lengths greater than 48 kbp.

The size and nature of the starting material (e.g., PCR products, 2 kb, 48 kb, mammalian genomic) affected the time dosages required to achieve desired shearing results (e.g., 4 minutes, 6 minutes, 8 minutes, etc.). Starting material greater than 3 micrograms was shown to require lower viscosity conditions of the sample prior to fragmentation. If the viscosity was not reduced, particularly for fragments greater than 500 bp, variation between samples were observed.

To reduce viscosity effects with long fragments, relatively short doses (e.g., 10% duty cycle, level 0.5 intensity, 200 cycles per burst) were helpful prior to the desired fragmentation dose. A duty cycle of 10%, level 0.5 intensity, and 1,000 cycles per burst for 3 seconds was also used for a short burst. For example, 5 micrograms per 100 microliters has been used with both linearized lambda and mammalian genomic DNA with short doses of 3 seconds. Different samples have required adjustment of time (e.g., 2, 3, 4, 5 seconds, etc.). The sample was slightly fragmented to allow flow of the fragments into the active acoustic zone, which is the bottom surface of the plug.

The vessel had a volume range of 50 to 100 microliters for DNA shearing and was designed for use at an intensity level of 5 or less. Upon volume reduction, duty cycle was reduced to less than 10%.

Generally, larger length starting materials (e.g., 100 kb) and larger masses (e.g., 5 micrograms) have required longer time doses. Circular DNA has required a short, high dose followed by a long, low dose to shear to a desired fragment size.

Example 4

Figure 16:
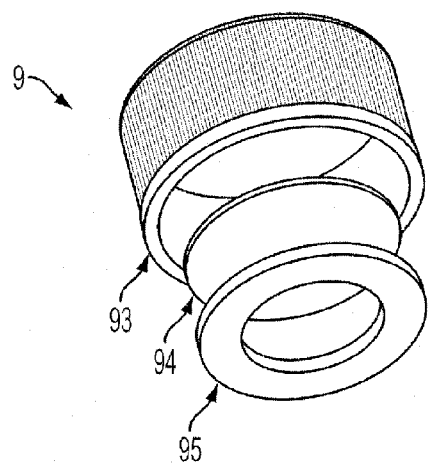
FIG. 16 shows an illustrative example of a cap used in Examples 4-7.

A test was done to compare the operation of a headspace control member that included a rigid surface presented at the sample interface in comparison to an arrangement in which the headspace control member included a relatively less rigid surface. A vessel and headspace control element arrangement similar to that in FIG. 2 was used for two device arrangements. However, the caps used for each of the two device arrangements were different. Both cap arrangements included a cover 93 like that shown in FIG. 16. That is, the cover 93 was arranged like a standard, plastic (polypropylene) vial cap capable of engaging with a cylindrically-shaped or threaded end of a glass vial, for example. In a first arrangement, the cap 9 included only the plastic cover 93. However, in a second arrangement, the cap 9 additionally included a metal plate 94 (or "head") and a liner 95, as shown in FIG. 16. The metal plate 94 was formed of a 1 mm thick stainless steel plate having a diameter approximately equal to the vial diameter and was adhered to the inner surface of the cover 93. The liner 95 was formed of a washer shaped plastic material was adhered to the metal plate 94. The vessels were glass vials having a total volume of 2 ml (in this example—other examples below involve larger volume vials) and the cap 9 was engaged with the vessel so that the undersurface of the cover 93 for the first arrangement or the metal plate 94 and liner 95 for the second arrangement were located at the sample interface. 20 microliters of 100 mM of Felodelpine (calcium channel blocker) in dimethylamine (DMA) was added to each vessel along with 1.98 milliliters of 0.2% polyvinylpyrrolidone and 0.25 mM Sodium Docecyl Sulfate in water.

Both device arrangements were acoustically treated using a Covaris S220X that was set to employ the following parameters: 350 peak incident power (PIP), a 40% duty factor (DF), 1000 cycles per burst (C/B), with the water coupling bath and sample at a 18 C temperature. The first test arrangement (lacking the metal plate) did not produce any crystalline particles after 20 minutes of processing using the above conditions. In contrast, the second test arrangement including the metal plate on the cap bottom produced crystalline nanoparticles.

Example 5

Similar to Example 4, a test was done to compare the operation of a headspace control member that included a rigid surface presented at the sample interface in comparison to an arrangement in which the headspace control member included a relatively less rigid surface. Two device arrangements like that described in Example 4 were used, where the vessel was a glass vial having a total volume of 2 ml. 1.9 ml of stabilization solution (0.1% SLS and 0.025% MC) was added to the vessels along with 10 mg of Quercetin, which resulted in a concentration of Quercetin of about 5 mg/ml. As in Example 4, the only difference between the two device arrangements was that in a first arrangement the lower end of the plastic cover was left unchanged, and in a second arrangement a plate of stainless steel having a thickness of about 0.5 to 1 mm and a diameter approximately equal to the diameter of the vial (about 12 mm) and a liner were attached to the lower end of the cover.

Both device arrangements were acoustically treated using a Covaris S220X that was set to employ the following parameters: 300 peak incident power (PIP), a 50% duty factor (DF), 200 cycles per burst (C/B), with the water coupling bath and sample at a 4 C temperature. The treatment devices (vessels and headspace control member) were treated for 5 minutes.

Figure 11:
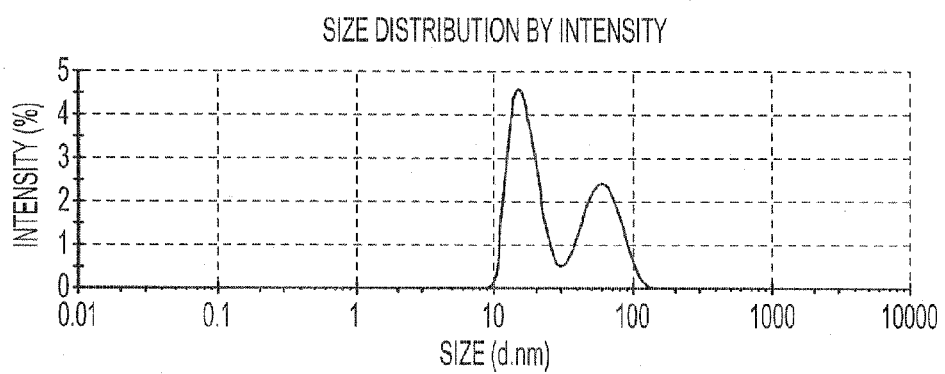
FIG. 11 shows a graph of particle sizes after treatment of a sample according to Example 5 in which a headspace control member lacks a rigid surface presented to the sample interface.
Figure 12:
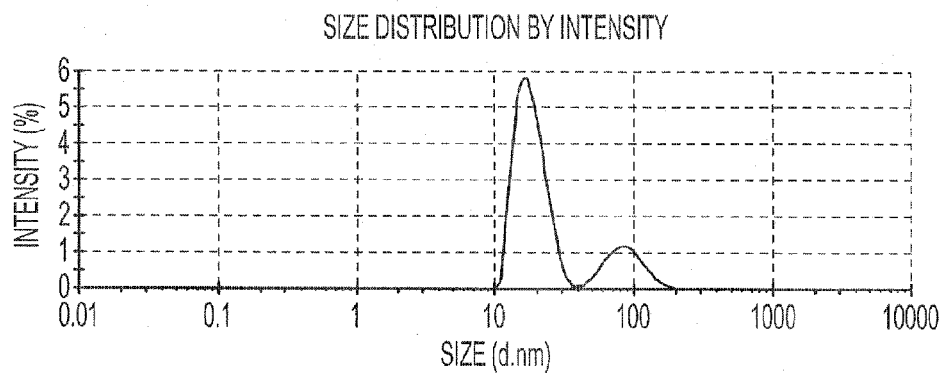
FIG. 12 shows a graph of particle sizes after treatment of a sample according to Example 5 in which a headspace control member includes a rigid surface presented to the sample interface.

FIG. 11 shows results of processing the first arrangement (including no metal surface at the cap bottom). Particles in the solution after processing had the following distribution: approximately 59% had a size of about 17 nm, whereas approximately 41% had a size of about 62 nm, giving a polydispersity index (PdI) of 0.255. However, as shown in FIG. 12, processing of the second arrangement (including a metal surface at the cap bottom) provided 79% of the particles with a size of 17 nm and 21% with a size of 89 nm, giving a PdI of 0.218. The results of these processes were surprising in that there was a 20% increase in the yield of 17 nm particles and a 50% reduction in 62 nm particles when using a headspace control member including a rigid metal surface presented to the interface. The higher concentration and reduced size of smaller particles in the second arrangement may be desirable in some cases, e.g., because smaller particles may exhibit improved stability and bioavailability.

In addition, it was noted that the cap including the metal surface did not heat up to the same extent as the cap lacking the metal surface. Moreover, the power output by the S220X machine for the arrangement including the metal surface remained generally stable during processing, whereas the power output varied significantly for the arrangement lacking the metal surface. (The S220X senses acoustic energy in and/or around the sample during processing, and adjusts the acoustic source output accordingly to maintain the target PIP at the sample. Variations in power output indicate variations in the intensity of the acoustic energy at the focal zone used to treat the sample. Thus, a more stable power output indicates that acoustic power applied to the sample remains relatively more stable over the course of processing and therefore that the total energy applied to the sample over the processing period is greater.)

Example 6

Similar to Example 4, a test was done to compare the operation of a headspace control member that included a rigid surface presented at the sample interface in comparison to an arrangement in which the headspace control member included a relatively less rigid surface. Two device arrangements like that described in Example 4 were used, where the vessel was a glass vial having a total volume of 18 ml. 17.82 ml of stabilization solution (0.1% SLS and 0.025% MC) was added to the vessels along with 0.18 ml of 100 mM Felodipine solution (Felodipine in dimethylamine—DMA). The only difference between the two device arrangements was that in a first arrangement the lower end of the plastic cover was left unchanged, and in a second arrangement a metal plate and liner were attached to the lower end of the cover.

Both device arrangements were acoustically treated using a Covaris S220X that was set to employ the following parameters: 350 peak incident power (PIP), a 40% duty factor (DF), 1000 cycles per burst (C/B), with the water coupling bath and sample at a 18 C temperature. The treatment devices (vessels and headspace control member) were treated for 11 minutes.

Figure 13:
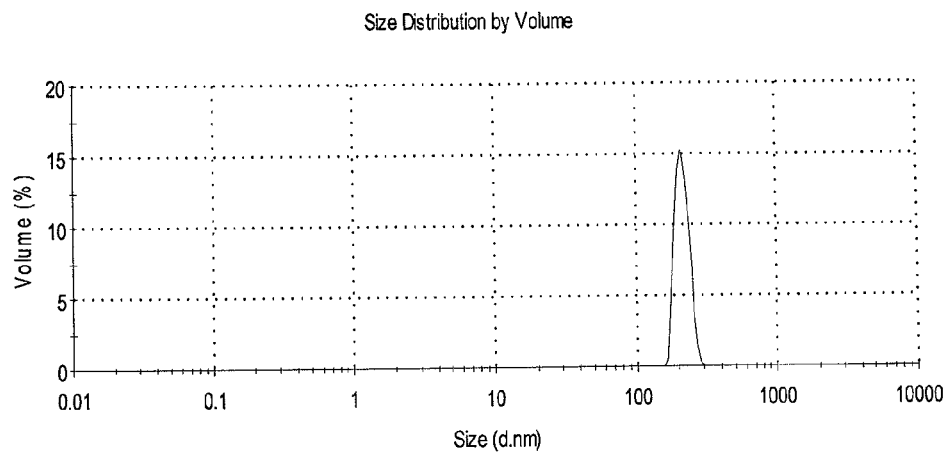
FIGS. 13 and 14 show results of Example 6.
Figure 14:
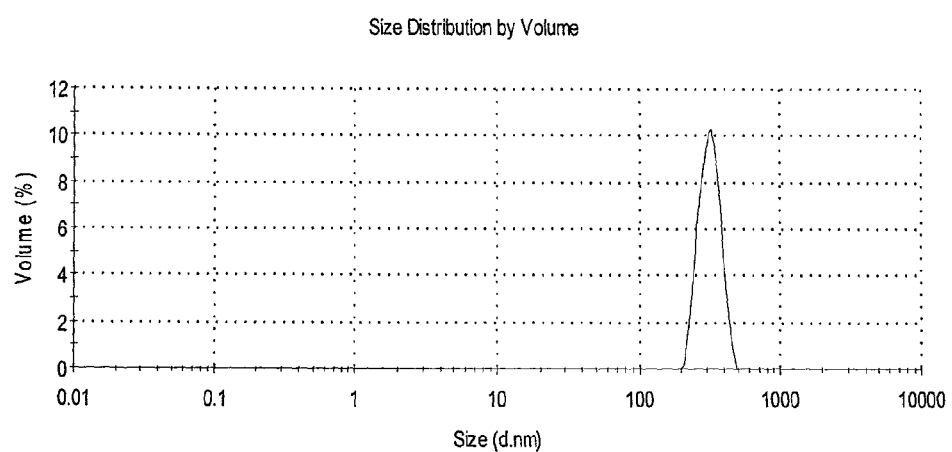

As shown in FIG. 13, the vessel that included the metal plate resulted in the production of clear, crystalline nanoparticles having a size of about 214 nm. However, the vessel that included only a plastic cover did not produce clear, crystalline nanoparticles, but rather only amorphous particles in a murky solution. FIG. 14 shows the result of processing the first arrangement (plastic cap only) for 20 minutes (i.e., 9 additional minutes as compared to the second device arrangement including the metal plate). It was found that crystalline particles having a size of about 313 nm were ultimately produced. Accordingly, the presence of the metal plate not only reduced the time to produce crystalline nanoparticles, but also resulted in a reduced particle size.

Example 7

Yet another example similar to Example 4 was performed to compare the operation of a headspace control member that included a rigid surface presented at the sample interface in comparison to an arrangement in which the headspace control member included a relatively less rigid surface. Two device arrangements like that described in Example 4 were used, where the vessel was a glass vial having a total volume of 12 ml. Slightly less than 12 ml ml of stabilization solution (0.1% SLS and 0.025% MC) was added to the vessels along with about 60 mg of Ibuprofen. The only difference between the two device arrangements was that in a first arrangement the lower end of the plastic cover was left unchanged, and in a second arrangement a metal plate and liner were provided.

Both device arrangements were acoustically treated using a Covaris S220X that was set to employ the following parameters: 150 peak incident power (PIP), a 50% duty factor (DF), 200 cycles per burst (C/B), with the water coupling bath and sample at a 3 C temperature. The treatment devices (vessels and headspace control member) were treated for intervals of 5, 15, 30 and 60 minutes.

Figure 15:
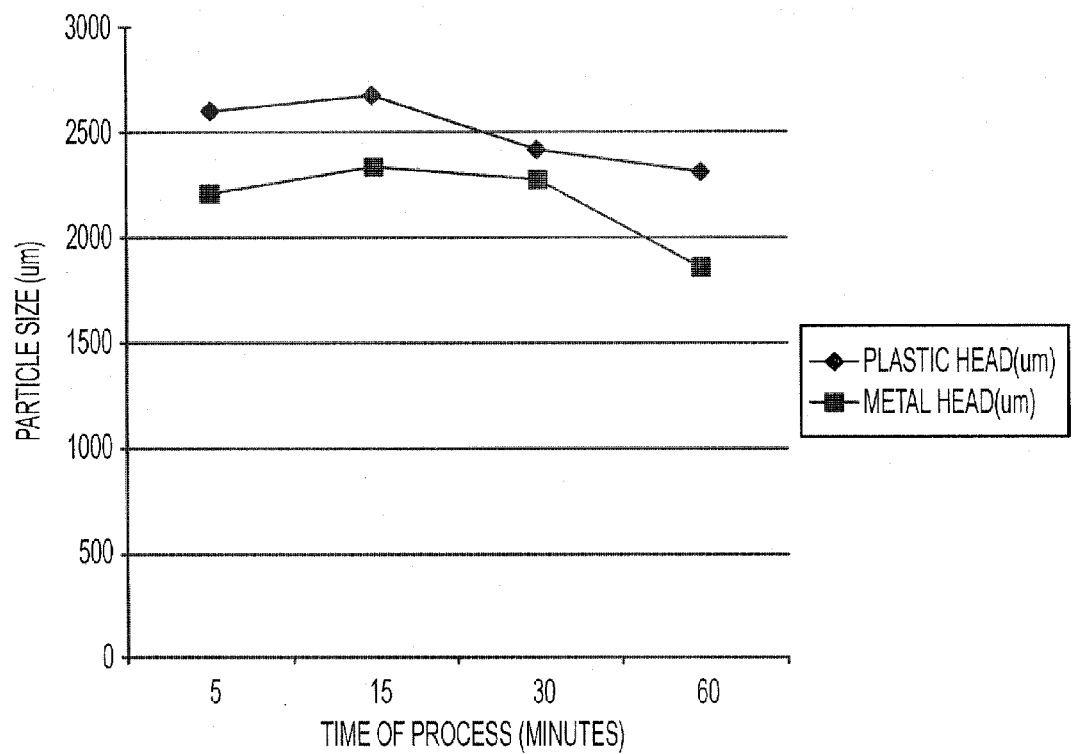
FIG. 15 shows results of Example 7.

As shown in FIG. 15, the vessel that included the metal plate resulted in the production of smaller particles than the vessel including a plastic cap only. Also, while it was noted that both vessels exhibited standing waves in the sample during processing, the headspace control element including the metal plate did not heat substantially, while the plastic cap only vessel experienced substantial heating of the cap.

As described above, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:
1. An acoustic treatment device, comprising:
a vessel having a total volume and arranged to hold a sample including a liquid having a sample volume that is less than the total volume and defining an interface between the sample and a gas;
an acoustic energy source for providing acoustic energy to the sample while the sample is in the vessel at a focal zone of the acoustic energy and is separated from the acoustic energy source;
a vessel holder arranged to support the vessel, the vessel holder adapted to position the vessel at a location at least partially in the focal zone of the acoustic energy;
a headspace control member that is positionable in the vessel to define a volume of a headspace near the interface, the headspace control member including a metal or ceramic element positionable adjacent the interface for reflecting acoustic energy, the headspace control member configured to allow gas to pass by when engaged with the vessel;
wherein the vessel and headspace control member are arranged for use with the acoustic energy source for providing acoustic energy to the sample while the sample is in the vessel at the focal zone of the acoustic energy and is separated from the acoustic energy source, wherein the metal or ceramic element is arranged on a side of the sample that is opposite the acoustic energy source such that the metal or ceramic element reflects acoustic energy in a direction toward the acoustic energy source.

2. The device of claim 1, wherein the metal or ceramic element includes a metal or ceramic plate having a thickness of about 0.5 to 1 mm.

3. The device of claim 1, further comprising the sample in the vessel, and wherein the metal or ceramic element is positioned in contact with the sample.

4. The device of claim 1, wherein the headspace control member is positioned relative to the vessel to define the headspace in the vessel near the interface to be 20% or less of the sample volume.

5. The device of claim 1, wherein the headspace control member is positioned relative to the vessel to define the headspace in the vessel near the interface to be 10% or less of the sample volume.

6. The device of claim 1, wherein the headspace control member is positioned relative to the vessel to define the headspace to be 0% of the sample volume.

7. The device of claim 1, wherein the headspace control member includes a distal end that is adjustably positionable in the vessel at or near the interface between the sample and the gas.

8. The device of claim 1, wherein the headspace control member includes a valve, a gas permeable membrane, a porous material, a filter, sponge, and/or an orifice, for allowing gas to pass through at least a portion of the headspace control member.

9. The device of claim 1, wherein the headspace control member is arranged to permit a pressure local to the sample in the vessel to equalize with an ambient pressure outside of the vessel.

10. The device of claim 1, wherein the headspace control member is arranged to reduce the headspace in the vessel to zero.

11. The device of claim 1, wherein the acoustic energy directed to the sample is sufficient to cause at least one of lysing, extraction, permeabilizing, stirring, catalyzing, degrading, fluidization, heating, particle breakdown, DNA shearing, or disruption of molecular bonds in the sample.

12. The device of claim 1, wherein the acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel.

13. The device of claim 1, wherein the headspace control member includes a cap arranged to engage with an opening of the vessel.

14. The device of claim 1, wherein the headspace control member includes a porous member positionable at or near the interface to define the volume of the headspace.

15. The device of claim 1, wherein the headspace control member acts as a nucleation site for cavitation in the liquid when the sample is subjected to the acoustic energy.

16. An acoustic treatment device, comprising:
a vessel having a total volume and arranged to hold a sample including a liquid having a sample volume that is less than the total volume and defining an interface between the sample and a gas;
a headspace control member that is positionable in the vessel to define a volume of a headspace near the interface, the headspace control member including a metal or ceramic element positionable adjacent the interface for reflecting acoustic energy, the headspace control member configured to allow gas to pass by when engaged with the vessel;
wherein the vessel and headspace control member are arranged for use with an acoustic energy source for providing acoustic energy to the sample while the sample is in the vessel at a focal zone of the acoustic energy and is separated from the acoustic energy source, wherein the metal or ceramic element is arranged on a side of the sample that is opposite the acoustic energy source such that the metal or ceramic element reflects acoustic energy in a direction toward the acoustic energy source.

17. The device of claim 16, wherein the metal or ceramic element includes a metal or ceramic plate having a thickness of about 0.5 to 1mm.

18. The device of claim 16, further comprising the sample in the vessel, and wherein the metal or ceramic element is positioned in contact with the sample.

19. The device of claim 16, wherein the headspace control member is positioned relative to the vessel to define the headspace in the vessel near the interface to be 20% or less of the sample volume.

20. The device of claim 16, wherein the headspace control member is positioned relative to the vessel to define the headspace in the vessel near the interface to be 10% or less of the sample volume.

21. The device of claim 16, wherein the headspace control member is positioned relative to the vessel to define the headspace to be 0% of the sample volume.

22. The device of claim 16, wherein the headspace control member includes a distal end that is adjustably positionable in the vessel at or near the interface between the sample and the gas.

23. The device of claim 16, wherein the headspace control member includes a valve, a gas permeable membrane, a porous material, a filter, sponge, and/or an orifice, for allowing gas to pass through at least a portion of the headspace control member.

24. The device of claim 16, wherein the headspace control member is arranged to permit a pressure local to the sample in the vessel to equalize with an ambient pressure outside of the vessel.

25. The device of claim 16, wherein the headspace control member is arranged to reduce the headspace in the vessel to zero.

26. The device of claim 16, wherein the headspace control member includes a cap arranged to engage with an opening of the vessel.

27. The device of claim 16, wherein the headspace control member includes a porous member positionable at or near the interface to define the volume of the headspace.

28. The device of claim 16, wherein the headspace control member acts as a nucleation site for cavitation in the liquid when the sample is subjected to the acoustic energy.

29. The device of claim 16, further comprising the acoustic energy source for providing acoustic energy to the sample while the sample is in the vessel at the focal zone of the acoustic energy and is separated from the acoustic energy source.

30. The device of claim 29, wherein the acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel.

31. The device of claim 16, wherein the acoustic energy directed to the sample is sufficient to cause at least one of lysing, extraction, permeabilizing, stirring, catalyzing, degrading, fluidization, heating, particle breakdown, DNA shearing, or disruption of molecular bonds in the sample.

32. The device of claim 16, further comprising a vessel holder arranged to support the vessel, the vessel holder adapted to position the vessel at a location at least partially in the focal zone of the acoustic energy.

* * * * *